United States Patent [19]

Monzen et al.

[11] Patent Number: 6,020,517
[45] Date of Patent: Feb. 1, 2000

[54] PROCESS FOR PRODUCTION OF BENZONITRILE AND BENZYL ALCOHOL

[75] Inventors: Hiroyuki Monzen; Katsutoshi Morinaka; Hideo Miyata; Tsutomu Nozawa; Haruaki Ito; Kohei Morikawa, all of Kawasaki, Japan

[73] Assignee: Showa Denko K.K., Tokyo, Japan

[21] Appl. No.: 09/065,043

[22] PCT Filed: Aug. 29, 1997

[86] PCT No.: PCT/JP97/03037

§ 371 Date: Apr. 27, 1998

§ 102(e) Date: Apr. 27, 1998

[87] PCT Pub. No.: WO98/08795

PCT Pub. Date: Mar. 5, 1998

[30] Foreign Application Priority Data

Aug. 29, 1996 [JP] Japan ................................. 8-229060

[51] Int. Cl.[7] .................... C07C 255/00; C07C 33/46; C07C 27/00
[52] U.S. Cl. ................... 558/425; 568/812; 568/814
[58] Field of Search ............... 558/425; 568/812, 568/814

[56] References Cited

U.S. PATENT DOCUMENTS 4,889,872  12/1989  Naumann et al. ............... 514/531

FOREIGN PATENT DOCUMENTS

| | | | |
|---|---|---|---|
| 3714602A1 | 11/1988 | Germany. | |
| 58-90523 | 5/1983 | Japan | C07C 33/46 |
| 59-184149 | 10/1984 | Japan | C07C 121/52 |
| 60-72850 | 4/1985 | Japan | C07C 121/50 |
| 61-218542 | 9/1986 | Japan | C07C 33/46 |
| 63-203649 | 8/1988 | Japan. | |
| 64-56656 | 3/1989 | Japan | C07C 121/52 |
| 2-104541 | 4/1990 | Japan | C07C 33/22 |
| 3-90057 | 4/1991 | Japan | C07C 255/50 |
| 4-89449 | 3/1992 | Japan | C07C 63/72 |
| 5-221898 | 8/1993 | Japan | C07C 33/46 |
| 7-165695 | 6/1995 | Japan | C07C 255/50 |

OTHER PUBLICATIONS (Abstract), Weigert, et al, "Hydrodecyanation", J. Mol. Cat., V. 75, N. 2, pp. 209–218, 1992.

*Primary Examiner*—Johann Richter
*Assistant Examiner*—Joseph Murray
*Attorney, Agent, or Firm*—Sughrue, Mion, Zinn, Macpeak & Seas, PLLC

[57] ABSTRACT

A process for producing a fluorinated benzonitrile comprising hydrogenolyzing a fluorinated dicyanobenzene substituted with 1 to 4 fluorine atoms and having the remainder which may be substituted with a chlorine atom in the presence of a catalyst to cause hydrodecyanation of only the cyano group of one side and a process for producing a fluorinated benzyl alcohol comprising reducing the fluorinated benzonitrile and hydrolyzing the fluorinated benzonitrile and reducing the resultant corresponding fluorinated benzoic acid to convert the cyano group to a hydroxymethyl group.

16 Claims, No Drawings

PROCESS FOR PRODUCTION OF BENZONITRILE AND BENZYL ALCOHOL

TECHNICAL FIELD

The present invention relates to a process for producing fluorinated benzonitrile and fluorinated benzyl alcohol useful as intermediates for the production of cyclopropane carboxylic acid esters having superior insecticidal action, and other agrochemicals, drugs, etc.

BACKGROUND ART

It has been disclosed that a cyclopropane carboxylic acid ester of a fluorinated benzyl alcohol having the general formula:

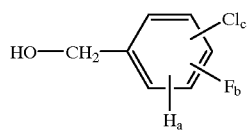

wherein a and b independently represent 1, 2, 3, or 4 and c represents 0, 1, or 2 has a high insecticidal activity (DE-A-2658074 etc.). In particular, it has been disclosed that a cyclopropane carboxylic acid ester of 2,3,5,6-tetrafluorobenzyl alcohol has a high insecticidal activity and that it has a lower toxicity to mammals compared with a cyclopropane carboxylic acid ester of pentafluorobenzyl alcohol, and therefore, is a superior insecticide (DE-A-3705224).

As a process for producing the fluorinated benzyl alcohol having the general formula (I), a process has been proposed of reducing a halogen substituted benzoic acid derivative with a metal hydrides such as $NaBH_4$, $LiAlH_4$. For example, DE-A-3714602 discloses a process for producing 2,3,5,6-tetrafluorobenzyl alcohol by reacting 2,3,5,6-tetrafluorobenzoic acid with $NaBH_4$ followed by treating with an alkylation agent. Further, DE-A-2658074, 2714042, and 2661074 disclose processes for producing for reducing polyfluorobenzoyl fluoride with $NaBH_4$ to produce polyfluorobenzyl alcohol and processes for reducing polyfluorobenzoyl fluoride with $LiAlH_4$ to produce a polyfluorobenzyl alcohol wherein one or more fluorine substituted groups are defluorinated. EP-A-31199 discloses a process for reacting 1,2,4,5-tetrafluorobenzene and n-butyl lithium and then reacting with carbon dioxide to form 2,3,5,6-tetrafluorobenzoic acid, which is reduced with $LiAlH_4$ to produce 2,3,5,6-tetrafluorobenzyl alcohol.

On the other hand, electrolytic reduction processes have also been proposed as processes for the production of a fluorinated benzyl alcohol having the general formula (I). For example, JP-A-1-119686 discloses a process for the production of 2,3,5,6-tetrafluorobenzaldehyde and 2,3,5,6-tetrafluorobenzyl alcohol by electrolytic reduction of pentafluorobenzoic acid using a solid metal or a solid alloy as a cathode and an aqueous solution of sulfuric acid, hydrochloric acid, phosphoric acid, or sulfonic acid as an electrolyte. Further, JP-A-63-206491 discloses production of 2,3,5,6-tetrafluorobenzyl alcohol as a mixture with pentafluorobenzyl alcohol so as to electrolytically reduce pentafluorobenzoic acid using a solid metal or solid alloy as a cathode and an aqueous sulfuric acid solution as an electrolyte. There are many reports on processes for production of a fluorinated benzyl alcohol by electrolytic reduction, but in the same way as above, a benzyl alcohol is produced as a mixture in each case ("J. Electroanal. Chem.", 1991, p. 215; "J. Electroanal. Chem.", 1987, p. 315; "J. Chem. Soc. Perkin Trans I", 1972, p. 189; "J. Appl. Electrochem.", 1992, p. 1082; "Denkikagaku oyobi Kogyobutsurikagaku", 1990, p. 83; etc.)

DISCLOSURE OF INVENTION

The object of the present invention is to produce a fluorinated benzyl alcohol having the general formula (I) and the intermediates thereof, the fluorinated benzonitrile having the general formula (III), by an industrially advantageous process at a high yield, more particularly, to produce 2,3,5,6-tetrafluorobenzonitrile and 2,3,5,6-tetrafluorobenzyl alcohol at a high purity and a high yield, which are useful as production intermediates of pyrethroids having a high insecticidal activity and a low toxicity to the human body.

In accordance with the present invention, there is provided a process for producing a fluorinated benzonitrile comprising the step of:

hydrogenolyzing a fluorinated dicyanobenzene substituted with 1 to 4 fluorine atoms and having the remainder which may be substituted with a chlorine atom in the presence of a catalyst so as to cause hydrodecyanation of only the cyano group of one side.

In accordance with the present invention, there is also provided a process for producing a fluorinated benzyl alcohol having the formula (I):

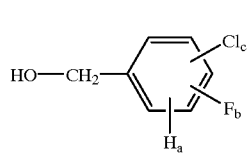

wherein a and b independently represent 1, 2, 3, or 4 and c represents 0, 1, or 2 comprising the steps of:

using a fluorinated dicyanobenzene having the formula (II)

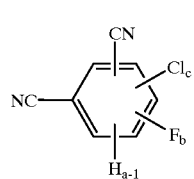

wherein a, b, and c are as defined above, as a starting material, and causing hydrodecyanation of only the cyano group of one side so as to produce a fluorinated benzonitrile having the formula (III):

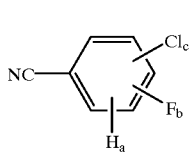

wherein a, b, and c are as defined above and then converting the cyano group of the fluorinated benzonitrile to a hydroxymethyl group to form the fluorinated benzonitrile to a hydroxymethyl group.

In accordance with the present invention, there is further provided a process for producing a fluorinated benzyl alcohol comprising reducing the above fluorinated benzonitrile, or hydrolyzing the fluorinated benzonitrile followed by reducing the resultant corresponding fluorinated benzoic acid, to convert the cyano group to a hydroxymethyl group.

Note that the fluorinated benzonitrile having the general formula (III) may specifically be reduced to a; a fluorinated benzaldehyde having the formula (IV):

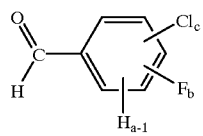

(IV)

wherein a, b, and c are as defined above, followed by reducing the aldehyde group of the fluorinated benzaldehyde to a hydroxymethyl group to form the fluorinated benzyl alcohol having the general formula (I).

Further, it is possible to reduce the cyano group of the fluorinated benzonitrile having the above formula (III) to a hydroxymethyl group by a single stage reaction without isolating the fluorinated benzaldehyde to obtain the fluorinated benzyl alcohol having the general formula (I).

BEST MODE FOR CARRYING OUT THE INVENTION

The present invention will now be explained in further detail. According to the present invention, it is possible to hydrogenolyze the fluorinated dicyanobenzene having the general formula (II) through the reaction formula (V) in the presence of a catalyst to hydrodecyanate only the cyano group of one side to produce a fluorinated benzonitrile having the general formula (III) and then carry out either one of the reactions shown in the reaction formulae (VI), (VII), and (VIII) to produce a fluorinated benzyl alcohol having the general formula (I):

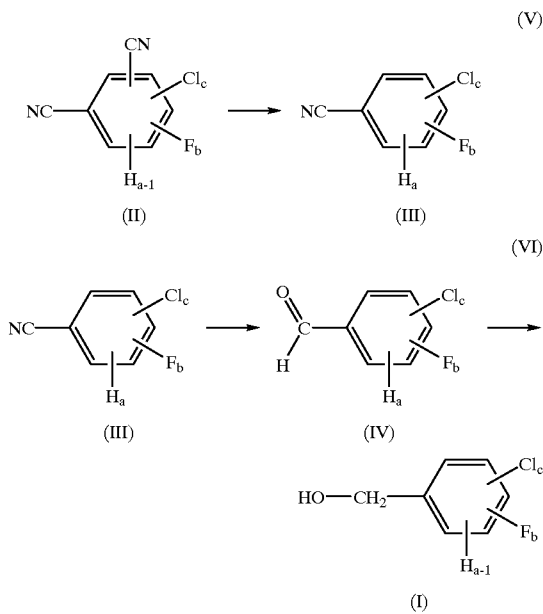

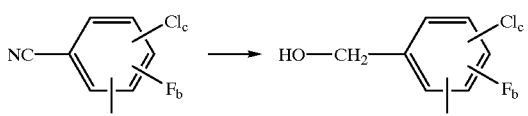

(VII)

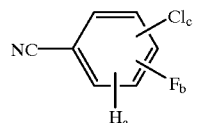

(VIII)

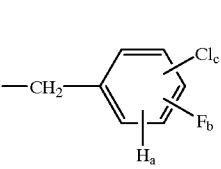

(I)

Thus, according to the process of the present invention, it is possible to produce the fluorinated benzyl alcohol having the general formula (I) by an industrially advantageous method at a high yield. It is particularly advantageous for the production of 2,3,5,6-tetrafluorobenzyl alcohol. That is, in the conventional electrolytic reduction process etc. of pentafluorobenzoic acid, inclusion or contamination of pentafluorobenzyl alcohol, which is the starting material of pyrethroids having a high toxicity to mammals, into the product is unavoidable. On the other hand, the process of the present invention uses tetrafluoroterephthalonitrile as a starting material and hydrodecyanates only one cyano group to produce 2,3,5,6-tetrafluorobenzonitrile, then converts the cyano group of the 2,3,5,6-tetrafluorobenzonitrile to a hydroxymethyl group to produce 2,3,5,6-tetrafluorobenzyl alcohol, and therefore, it is possible to completely avoid production of pentafluorobenzyl alcohol.

For the starting material of the present invention, it is possible to use the fluorinated dicyanobenzene having the general formula (II). Specifically, 2,3,5,6-tetrafluoroterephthalonitrile, 3,4,5,6-tetrafluorophthalonitrile, 2,4,5,6-tetrafluoroisophthalonitrile, 2,3,5-trifluoroterephthalonitrile, 2,6-difluoroterephthalonitrile, 2,6-difluoro-3,5-dichloroterephthalonitrile, 2,3-difluoro-5-chloroterephthalonitrile, 2-fluoro-3,5-dichloroterephthalonitrile, etc. may be used. In particular, a 2,3,5,6-tetrafluoroterephthalonitrile of general formula (II) having a=1, b=4, and c=0 is preferably used. These fluorinated dicyanobenzenes may be produced by known methods. For example, it is possible to produce the fluorinated dicyanobenzenes by replacing the chlorine atoms of chlorinated dicyanobenzenes obtained by chlorination of dicyanobenzenes with fluorine by a fluorinated alkali. More specifically, JP-B-44-28493 discloses a process for producing 2,3,5,6-tetrafluoroterephthalonitrile by reacting 2,3,5,6-tetrachloroterephthalonitrile with potassium fluoride.

D. J. Milner reports the reaction of tetrafluoroterephthalonitrile with methyl magnesium bromide to synthesize 4-methyl-2,3,5,6-tetrafluorobenzonitrile (J. Organometallic Chem., 302 (1986) 147). In this case, 2,3,5,6-tetrafluorobenzonitrile is obtained as a byproduct, but the yield thereof is extremely low. Further, this reaction requires equal moles of a Grignard reagent such as methyl magnesium bromide and the handling is also difficult, and therefore, this cannot be said to be an industrially advantageous process as a process for producing 2,3,5,6-tetrafluorobenzonitrile.

The hydrodecyanation reaction according to the present invention is carried out in the presence of a catalyst by the hydrogenolysis shown in the reaction formula (V).

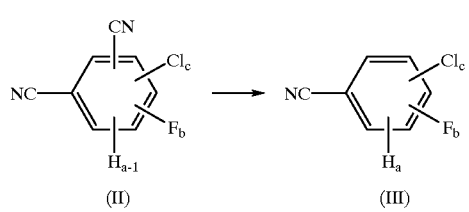

In the present invention, as the decyanation catalyst, at least one metal catalyst selected from metals of the Group VIII, Group IX, and Group X of the Periodic Table such as palladium, platinum, nickel, ruthenium, rhodium may be used. In particular, palladium, platinum, and nickel may be suitably used. The catalyst may be used as it is as a metal or in the form of a supported catalyst. As the carrier of the supported catalyst, activated carbon, silica, alumina, and the like may be used. As specific examples of the preferable catalyst, palladium/activated carbon, palladium/silica, etc. may be mentioned.

In the present invention, the pretreating method of the catalyst in advance in a hydrogen atmosphere is an effective means for the activation of the catalyst. The pretreating method is not particularly limited, but the method of holding the catalyst at a temperature from room temperature to about 400° C. in a hydrogen flow or in a hydrogen atmosphere is mentioned.

Further, the addition of a co-catalyst (or a catalyst promoter) is effective for the reaction of the present invention and improves the reaction rate and the selectivity. As such a co-catalyst, amine compounds such as ethylamine, triethylamine, chelate compounds such as ethylenediaminetetraacetic acid, nitrilotriacetic acid, 1,2-diaminopropanetetraacetic acid, 1,3-diamino-2-propanoltetraacetic acid, bis(2-aminoethyl)ethyleneglycoltetraacetic acid, and their alkali salts; carboxylic acid compounds such as acetic acid, formic acid; metal salts such as lead acetate may be used. In particular, the addition of chelate compounds such as ethylenediaminetetraacetic acid, nitrilotriacetic acid, and alkali salts thereof improve the reaction rate and the selectivity, and therefore, these are preferably used as co-catalysts.

As the reaction solvents in the reaction of the present invention, it is possible to use a relatively broad range of solvents. For example, aromatic hydrocarbons such as benzene, toluene, ethylbenzene, cumene, tert-butylbenzene, xylene, mesitylene; aliphatic hydrocarbons such as hexane, cyclohexanes; alcohols such as methanol, 2-propanol; ethers such as tetrahydrofuran, 1,4-dioxane, diethylene glycol dimethyl ether; carboxylic acids such as acetic acid, formic acid; nitriles such as acetonitrile, etc. may be used. In particular, monoalkyl substituted benzenes such as toluene, ethylbenzene, cumene, tert-butylbenzene are preferably used. Further, when using a reaction of a fixed bed gas phase process, the reaction can be carried out in the absence of a solvent.

The type of the reaction is not particularly limited, but the liquid phase suspension bed process, fixed bed gas phase process, liquid phase fixed bed process, or batch process may be used.

The reaction temperature is not particularly limited, but it is preferably to use a temperature from room temperature to about 400° C. In particular, when using a reaction of the fixed bed gas phase process, it is preferable to react at a temperature of 200° C. or more. Further, the reaction pressure may be in the range of atmospheric pressure to a higher pressure. The hydrogen partial pressure is preferably in the range of 1 MPa or less.

The hydrogen in the hydrodecyanation reaction may be supplied as it is or in the form of a mixture with nitrogen gas. Note that the supply of hydrogen gas is not essential. For example, it is also possible not to supply hydrogen gas, but an aromatic compound having hydrogen at the α-position can be used as a hydrogen source. For example, if the reaction is carried out in the presence of a monoalkyl substituted benzene such as toluene, ethylbenzene, cumene in an inert gas atmosphere, it is possible to simultaneously produce benzyl cyanides useful as materials for synthesis of drugs together the fluorinated benzonitrile by the transcyanation reaction shown by the reaction formula (IX):

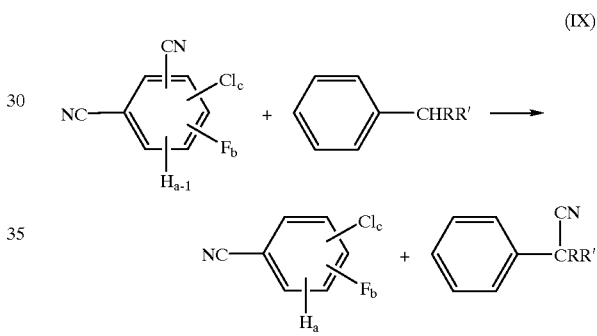

wherein a, b, and c are as defined above and R and R' are independently a hydrogen atom or an alkyl group.

The fluorinated benzonitrile having the general formula (III) obtained by the above reaction may be purified by separating the catalyst by filtration, centrifugation, decantation, and other operations, followed by distillation etc. Further, it is also possible to use the reaction mixture for the next step as it is, without purification. For example, it is possible to supply the reaction mother solution, from which the catalyst is separated, to the next step and carry out the reaction for converting the cyano group to a hydroxymethyl group.

The fluorinated benzonitrile having the general formula (III) is converted to the fluorinated benzyl alcohol having the general formula (I) by any reaction of the reaction formulae (VI), (VII), and (VIII):

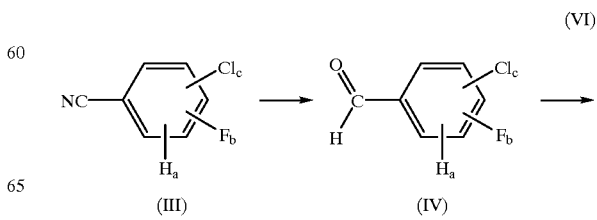

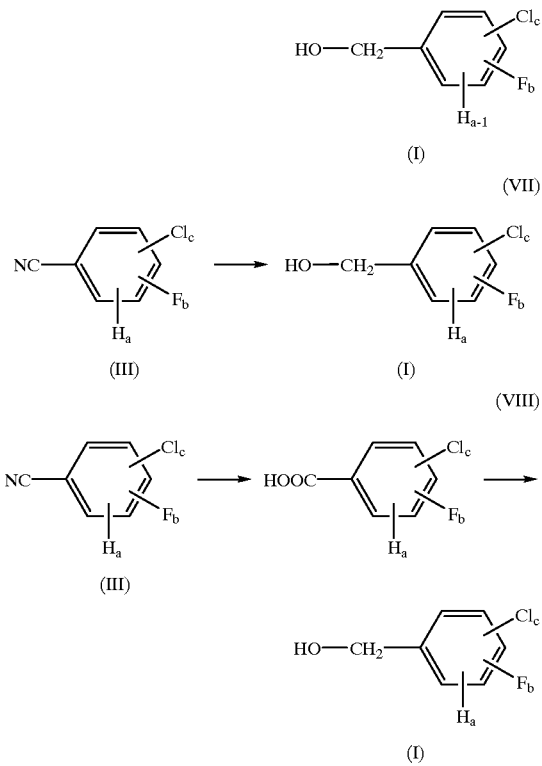

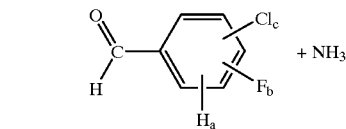

According to the reaction formula (VI), it is possible to reduce the fluorinated benzonitrile having the general formula (III) to the fluorinated benzaldehyde having the general formula (IV), then reduce the aldehyde group to a hydroxymethyl group to produce the fluorinated benzyl alcohol having the general formula (I).

The preparation for the fluorinated benzaldehyde is carried out by hydrogen reduction in the presence of a catalyst. This reaction proceeds according to the mechanism of the reaction formulae (X) and (XI). That is, hydrogen is added to the cyano group and the corresponding imine is produced. The reaction intermediate imine is hydrolyzed to synthesize the aldehyde.

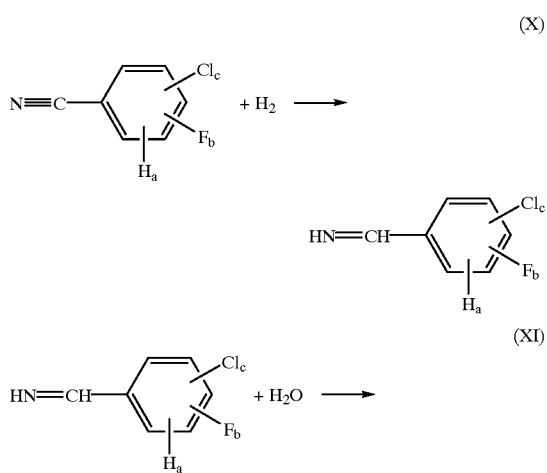

This reaction is carried out in the presence of a catalyst. As the catalyst, any one of metal catalysts selected from the Group VIII, Group IX, and Group X of the Periodic Table such as nickel, palladium, platinum may be used. In particular, it is possible to preferably use a nickel or palladium catalyst. These catalysts may be used as they are as metals or in the form of a supported catalyst. As the support, activated carbon, silica, alumina, and the like may be used. As specific examples of preferable catalysts, Raney nickel, palladium/activated carbon, etc. may be exemplified.

The addition of a co-catalyst is effective for this reaction. Salts or oxides of lead, cadmium, antimony, bismuth, zinc, iron, and copper may be used as the co-catalyst. In particular, copper compounds such as copper acetate and lead compounds such as lead acetate, are effective for suppressing the production of by-products such as amines. Further, the addition of an acid is effective for this reaction. It is believed that the acid promotes the hydrolysis reaction of (XI), and therefore, suppresses the production of the byproduct amines resulting from the excessive reduction of the imines produced by the reaction of (X). As the acid, formic acid, acetic acid, monochloroacetic acid, dichloroacetic acid, trifluoroacetic acid, sulfuric acid, hydrochloric acid, phosphoric acid, and the like may be used. In particular, chloroacetic acids, fluoroacetic acids, formic acid, and acetic acid may be preferably used.

As the solvent of the reaction, alcohols such as methanol, ethanol, 2-propanol, ethers such as 1,4-dioxane, tetrahydrofuran, and carboxylic acids such as acetic acid, formic acid may be used. In particular, methanol and acetic acid are preferably used. Further, the amount of the water added is preferably in the range of 1 to 1000 times molar amount relative to the raw material.

The form of the reaction is not particularly limited, but the liquid phase suspension bed process, fixed bed gas phase process, liquid phase fixed bed process, or batch process may be used.

The reaction temperature is not particularly limited, but it is preferably to use a temperature from ordinary temperature to about 200° C. The reaction pressure may be in the range of atmospheric pressure to a higher pressure. The hydrogen partial pressure is preferably in the range of 0.1 MPa or less.

The fluorinated benzaldehyde having the general formula (IV) obtained by the above reaction may be purified by separating the catalyst by filtration, centrifugation, decantation, and other operations, then distillation etc. Further, it is also possible to use the reaction product for the next step as it is, without purification. For example, it is possible to supply the reaction mother solution, from which the catalyst is separated, to the next step and carry out the reaction for converting the aldehyde group to the corresponding hydroxymethyl group.

The benzaldehyde having the general formula (IV) produced by the above reaction is converted to the benzyl alcohol having the general formula (I) shown by the reduction reaction of the reaction formula (XII).

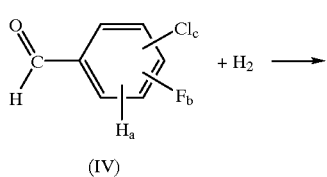

(IV)

+ H₂ ⟶

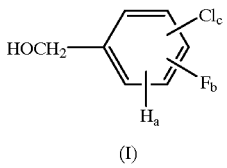

(I)

The reaction proceeds in the presence of a metal catalyst such as nickel, palladium, platinum, ruthenium, cobalt, copper. In particular, it is possible to preferably use a nickel, palladium, or platinum catalyst. These catalysts may be used as they are as metals or in the form of supported catalysts. As the support, activated carbon, silica, alumina, and the like may be used. As specific examples of preferable catalysts, Raney nickel, palladium/activated carbon, etc. may be mentioned. Further, metal hydrides such as $NaBH_4$, $LiAlH_4$, may be used to reduce the aldehyde to the alcohol.

As the reaction solvent, alcohols such as methanol, ethanol, 2-propanol, ethers such as 1,4-dioxane, tetrahydrofuran, carboxylic acids such as acetic acid, formic acid may be used. In particular, methanol is preferably used.

The form of the reaction is not particularly limited, but the liquid phase suspension bed process, fixed bed gas phase process, liquid phase fixed bed process, or batch process may be used.

The reaction temperature is not particularly limited, but it is preferably to use a temperature from ordinary temperature to about 100° C. The reaction pressure may be in the range of atmospheric pressure to a higher pressure. The hydrogen partial pressure is preferably in the range of 1 MPa or less.

The benzyl alcohol having the general formula (I) obtained by the above reaction may be purified by separating the catalyst by filtration, centrifugation, decantation, and other operations, then distillation etc.

Next, the method of direct reduction of the cyano group of the benzonitrile having the general formula (III) to a hydroxymethyl group by the reaction of the reaction formula (VII) to produce the benzyl alcohol having the general formula (I) will now be explained.

This reaction is shown by the reaction formula (XIII). The mechanism of this reaction resides in the successive proceedings of each element reaction, i.e., the production of imines by the reduction of the cyano group in the reaction formula (X), the production of aldehydes by hydrolysis of imine of the reaction formula (XI), and the production of alcohol by the reduction of the aldehyde of the reaction formula (XII).

(XIII)

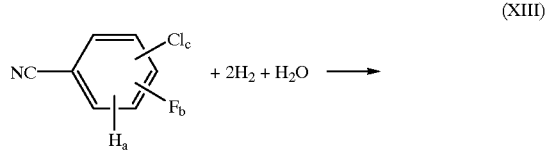

+ 2H₂ + H₂O ⟶

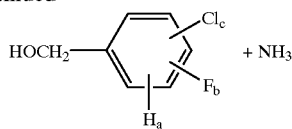

+ NH₃

The production process of the benzyl alcohol having the general formula (I) according to this reaction is the most superior process in the point that the process is tremendously simplified.

The reaction proceeds in the presence of a catalyst. As the catalyst, at least one metal catalyst selected from the group consisting of metals of the Group VIII, Group IX, and Group X of the Periodic Table such as nickel, palladium, platinum, may be used. In particular, it is possible to preferably use a nickel catalyst. These catalysts may be used as they are as metals or in the form of supported catalysts. As the support, activated carbon, silica, alumina, and the like may be used. As specific examples of preferable catalysts, Raney nickel may be mentioned.

Addition of a co-catalyst is effective for this reaction. Salts or oxides of lead, cadmium, antimony, bismuth, zinc, iron, and copper may be used as the co-catalyst. In particular, copper compounds such as copper acetate and lead compounds such as lead acetate are effective for suppressing the production of by-products such as amines. Further, the addition of an acid is effective for this reaction. As the acid, formic acid, acetic acid, monochloroacetic acid, dichloroacetic acid, trifluoroacetic acid, sulfuric acid, hydrochloric acid, phosphoric acid, and the like may be used, but especially, chloroacetic acids, fluoroacetic acids, formic acid, and acetic acid may be preferably used.

As the solvent of the reaction, alcohols such as methanol, ethanol, 2-propanol, ethers such as 1,4-dioxane, tetrahydrofuran, carboxylic acids such as acetic acid, formic acid, may be used. In particular, methanol is preferably used. Further, the amount of the water added is preferably in the range of 1 to 1000 times molar amount relative to the raw material.

The form of the reaction is not particularly limited, but the liquid phase suspension bed process, fixed bed gas phase process, liquid phase fixed bed process, or batch process may be used.

The reaction temperature is not particularly limited, but it is preferably to use a temperature from ordinary temperature to about 200° C. The reaction pressure may be in the range of atmospheric pressure to a higher pressure. The hydrogen partial pressure is preferably in the range of 1 MPa or less.

The benzyl alcohol having the general formula (I) obtained by the reaction may be purified by separating the catalyst by filtration, centrifugation, decantaiton, and other operations, then distillation etc.

Further, it is possible to hydrolyze the cyano group of the benzonitrile having the general formula (III) to a carboxyl group by the reaction having the reaction formula (VIII) and then reduce the carboxyl group to a hydroxymethyl group to produce the benzyl alcohol having the general formula (I).

The reaction for hydrolyzing the cyano group to convert it to a carboxyl group proceeds in the presence of an acid or alkali according to known reactions. In the present invention, it is also possible to use an acid or alkali to hydrolyze the general formula (III) to form benzoic acid, but an acid is preferably used to prevent the simultaneous occurrence of hydrolysis of the fluoro substituted group. As the preferably used acids, sulfuric acid, hydrochloric acid, nitric acid, and the like may be mentioned.

By reducing the carboxyl group of the obtained benzoic acids to hydroxymethyl groups, the benzyl alcohol having the general formula (I) is produced. This reduction reaction is a known reaction. For example, it is performed using metal hydrides such as $NaBH_4$, $LiAlH_4$. More specifically, DE-A-3714602 discloses a process of reacting 2,3,5,6-tetrafluorobenzoic acid with $NaBH_4$ to produce 2,3,5,6-benzyl alcohol.

EXAMPLES

The present invention will now be explained in detail by Examples, but the scope of the present invention is of course not limited to these Examples.

Example 1
(Hydrodecyanation Reaction)

100 g of toluene, 0.20 g of 5% palladium/activated carbon, and 1.0 g of 2,3,5,6-tetrafluoroterephthalonitrile were added to a 500 cc glass three-necked flask with a reflux condenser in a nitrogen atmosphere. The gas phase was sufficiently substituted by hydrogen gas, then a hydrogen balloon was attached to the top portion of the reflux condenser and the resulting mixture was heated to 100° C. After 8 hours reaction, the reaction solution was analyzed by gas chromatography, whereupon the rate of conversion of 2,3,5,6-tetrafluorotetraphthalonitrile was found to be 98%, the yield of 2,3,5,6-tetrafluorobenzonitrile (based on 2,3,5,6-tetrafluoroterephthalonitrile) was 73%.

Example 2
(Hydrodecyanation Reaction)

Using a method similar to Example 1 and using 75 g of formic acid, 5.0 g of Raney nickel, and 2.5 g of 2,3,5,6-tetrafluoroterephthalonitrile, a reaction was carried out at 80° C. for 30 minutes. The conversion of 2,3,5,6-tetrafluoroterephthalonitrile was found to be 82% and the yield of 2,3,5,6-tetrafluorobenzonitrile (based on 2,3,5,6-tetrafluoroterephthalonitrile) was 35%.

Example 3
(Hydrodecyanation Reaction)

A reaction was carried out in the same way as in Example 1, except that 1.0 g of triethylamine was added as a co-catalyst and the reaction time was made 7 hours. The conversion of 2,3,5,6-tetrafluoroterephthalonitrile was found to be 100% and the yield of 2,3,5,6-tetrafluorobenzonitrile was 77%.

Example 4
(Hydrodecyanation Reaction)

By a method similar to Example 1 and using 125 g of diethyleneglycol dimethyl ether and 1.60 g of 5% palladium/activated carbon, a reaction was carried out at 100° C. for 1.5 hours. The conversion of 2,3,5,6-tetrafluoroterephthalonitrile was found to be 100% and the yield of 2,3,5,6-tetrafluorobenzonitrile (based on 2,3,5,6-tetrafluoroterephthalonitrile) was 37%.

Example 5
(Hydrodecyanation Reaction)

A reaction was carried out in the same way as in Example 4, except that 100 g of 2-propanol was used as the solvent and the reaction time was made 3 hours. The conversion of 2,3,5,6-tetrafluoroterephthalonitrile was found to be 89% and the yield of 2,3,5,6-tetrafluorobenzonitrile (based on 2,3,5,6-tetrafluoroterephthalonitrile) was 38%.

Example 6
(Hydrodecyanation Reaction)

By a method similar to Example 1 and using 100 g of toluene, 1.00 g of 5% palladium/activated carbon, 0.70 g of ethylenediaminetetraacetic acid, and 5.0 g of 2,3,5,6-tetrafluoroterephthalonitrile, a reaction was carried out at 100° C. for 22 hours. The conversion of 2,3,5,6-tetrafluoroterephthalonitrile was found to be 95% and the yield of 2,3,5,6-tetrafluorobenzonitrile (based on 2,3,5,6-tetrafluoroterephthalonitrile) was 81%.

Example 7
(Hydrodecyanation Reaction)

115 g of toluene, 1.60 g of 5% palladium/activated carbon, 1.20 g of formic acid, and 1.0 g of 2,3,5,6-tetrafluoroterephthalonitrile were added to a 500 cc stainless steel autoclave equipped with a Teflon inner tube in a nitrogen atmosphere. The gas phase was sufficiently replaced with hydrogen gas, then the autoclave was sealed and heated to 150° C. After 2 hours, the reaction solution was analyzed by gas chromatography, whereupon the conversion of 2,3,5,6-tetrafluoroterephthalonitrile was found to be 99% and the yield of 2,3,5,6-tetrafluorobenzonitrile (based on 2,3,5,6-tetrafluoroterephthalonitrile) was 63%.

Example 8
(Hydrodecyanation Reaction)

200 g of ethylbenzene, 0.30 g of 5% palladium/activated carbon, and 6.0 g of 2,3,5,6-tetrafluoroterephthalonitrile were added to a 1000 cc stainless steel autoclave in a nitrogen atmosphere. The gas phase was sufficiently replaced with a mixed gas of 41 vol % hydrogen and 59 vol % nitrogen, then the mixed gas was used to keep the pressure at 0.23 MPa and the temperature was maintained at 190° C. After 2, 4, and 6 hours, the reaction solution was analyzed by gas chromatography, whereupon the conversions of 2,3,5,6-tetrafluoroterephthalonitrile were found to be 23, 62, and 99% and the yields of 2,3,5,6-tetrafluorobenzonitrile (based on 2,3,5,6-tetrafluoroterephthalonitrile) were 22, 56, and 87%, respectively.

Example 9
(Hydrodecyanation Reaction) 120 of ethyl benzene, 0.67 g of 5% palladium/activated carbon, 13.9 g of 2,3,5,6-tetrafluoroterephthalonitrile were added to a 300 cc stainless steel autoclave equipped with a reflux condenser in a nitrogen atmosphere. The gas phase was sufficiently replaced with mixed gas of 41 vol % hydrogen and 59 vol % nitrogen, then the mixed gas was used to maintain the pressure at 0.23 MPa and the temperature was maintained at 190° C. During the reaction, the pressure was held at 0.23 MPa while circulating the above mixed gas at a flow rate of 15 to 30 cc/min. After 21 hours, the reaction solution was analyzed by gas chromatography, whereupon the conversion of 2,3,5,6-tetrafluoroterephthalonitrile was found to be 91% and the yield of 2,3,5,6-tetrafluorobenzonitrile (based on 2,3,5,6-tetrafluoroterephthalonitrile) was 73%.

Example 10
(Hydrodecyanation Reaction)

100 g of ethylbenzene and 3.0 g of 5% palladium/activated carbon were added to a 1000 cc stainless steel autoclave. The gas phase was sufficiently replaced with hydrogen gas, then hydrogen gas was used to apply a pressure of 0.3 MPa and make the temperature 100° C. and catalytic pretreatment was carried out for 1 hour. The gas phase was again sufficiently replaced with nitrogen, then 3.0 g of the reaction material, that is, 2,3,5,6- tetrafluoroterephthalonitrile was added. The nitrogen atmosphere was maintained, the autoclave sealed as it was at atmospheric pressure, and the temperature held at 175° C. After 3 hours, the reaction solution was analyzed by gas chromatography, whereupon the conversion of 2,3,5,6-tetrafluoroterephthalonitrile was found to be 100% and the yield of 2,3,5,6-tetrafluorobenzonitrile (based on 2,3,5,6-tetrafluoroterephthalonitrile) was 95%. At the same time, 13.4 mmol of α-methylbenzylcyanide was produced. This corresponded to 0.95 times molar amount relative to the production of 2,3,5,6-tetrafluorobenzonitrile.

Example 11
(Hydrodecyanation Reaction)

By a method similar to Example 10 and using 6.0 g of 5% palladium/activated carbon and 3.0 g of 3,4,5,6-tetrafluorophthalonitrile, a reaction was carried out at 150° C. After 5 hours, the reaction solution was analyzed by gas chromatography, whereupon the conversion of 3,4,5,6-tetrafluorophthalonitrile was found to be 12% and the yield of 2,3,4,5-tetrafluorobenzonitrile (based on 3,4,5,6-tetrafluorophthalonitrile) was 6%. At the same time, 0.3 mmol of α-methylbenzylcyanide was produced. This corresponded to 0.3 times molar amount relative to the production of 2,3,4,5-tetrafluorobenzonitrile times.

Example 12
(Hydrodecyanation Reaction)

By a method similar to Example 11, a reaction was carried out using 2,4,5,6-tetrafluoroisophthalonitrile, instead of 3,4,5,6-tetrafluorophthalonitrile. After 5 hours, the reaction solution was analyzed by gas chromatography, whereupon the conversion of 2,4,5,6-tetrafluoroisophthalonitrile was found to be 36% and the yield of 2,3,4,6-tetrafluorobenzonitrile (based on 2,4,5,6-tetrafluoroisophthalonitrile) was 20%. At the same time, 1.1 mmol of α-methylbenzylcyanide was produced. This corresponded to 0.35 times molar amount relative to the production of 2,3,4,6-tetrafluorobenzonitrile.

Example 13
(Hydrodecyanation Reaction)

4.5 g of granulated 5% palladium/activated carbon was packed in a stainless steel reaction tube having an inside diameter of 16 mm, the temperature of the catalyst layer was held at 100° C., and the hydrogen gas was circulated for 1 hour at a flow rate of 100 cc/min for catalytic preprocessing. The hydrogen gas was supplied at a flow rate of 6 cc/min and the nitrogen gas at 100 cc/min and the temperature of the catalyst layer was made 250° C. A toluene solution containing 1.7% by weight of 2,3,5,6-tetrafluoroterephthalonitrile was supplied to the reaction tube by a pump at a flow rate of 70 to 73 g/hr.

The gas distilled off from the reaction tube was condensed and collected in a cooling tube. The condensate captured from one hour to one and a half hours after the start of the supply of the material was analyzed, whereupon the conversion of 2,3,5,6-tetrafluoroterephthalonitrile was found to be 100% and the yield of 2,3,5,6-tetrafluorobenzonitrile (based on 2,3,5,6-tetrafluoroterephthalonitrile) was 77%.

Example 14
(Reaction for Conversion from Cyano Group to Aldehyde Group)

0.5 g of Raney nickel, 0.31 g of a copper acetate 10 hydrate, and 50 ml of water were added to a 500 cc glass three-necked flask with a reflux condenser in a nitrogen atmosphere. The resulting mixture was stirred at 25° C. for 2 hours, then 50 ml of water and methanol were successively added and decanting performed to wash the catalyst. Further, 80 g of methanol, 100 g of acetic acid, and 5 g of water as the solvent and 8.75 g of 2,3,5,6-tetrafluorobenzonitrile were newly added. The gas phase was sufficiently replaced with hydrogen gas, then a hydrogen balloon was attached to the top portion of the reflux condenser and the reaction carried out at 25° C. for 6 hours. The reaction solution was analyzed by gas chromatography, whereupon the conversion of 2,3,5,6-tetrafluorobenzonitrile was found to be 100%, the yield of 2,3,5,6-tetrafluorobenzaldehyde (based on 2,3,5,6-tetrafluorobenzonitrile) was 80%, and the yield of 2,3,5,6-tetrafluorobenzyl alcohol was 2%.

Example 15
(Reaction for Conversion from Cyano Group to Aldehyde Group)

150 g of acetic acid, 50 g of 3N aqueous sulfuric acid solution, 0.875 g of 2% palladium/activated carbon, and 8.75 g of 2,3,5,6-tetrafluorobenzonitrile were added to a 500 cc glass three-necked flask with a reflux condenser in a nitrogen atmosphere. The gas phase was sufficiently replaced with hydrogen gas, then a hydrogen balloon was attached to the top portion of the reflux condenser and the reaction was carried out at 80° C. for 8 hours. The reaction solution was analyzed by gas chromatography, whereupon the conversion of 2,3,5,6-tetrafluorobenzonitrile was found to be 59%, the yield of 2,3,5,6-tetrafluorobenzaldehyde (based on 2,3,5,6-tetrafluorobenzonitrile) was 33%, and the yield of 2,3,5,6-tetrafluorobenzyl alcohol was 7%.

Example 16
(Reaction for Conversion from Cyano Group to Aldehyde Group)

Using 158 g of methanol, 5.7 g of concentrated sulfuric acid, and 5.0 g of Raney nickel, a reaction was carried out by a method similar to Example 15. When the reaction was carried out at 25° C. for 4 hours, the conversion of 2,3,5,6-tetrafluorobenzonitrile was found to be 80%, the yield of 2,3,5,6-tetrafluorobenzaldehyde (based on 2,3,5,6-tetrafluorobenzonitrile) was 44%, and the yield of 2,3,5,6-tetrafluorobenzyl alcohol was 1%.

Example 17
(Reaction for Conversion from Cyano Group to Aldehyde Group)

Using 83 g of methanol, 21 g of water, 45 g of formic acid, 1.5 g of Raney nickel, and 5.0 g of 2,3,5,6-tetrafluorobenzonitrile, a reaction was carried out by a method similar to Example 15. When the reaction was carried out at 60° C. for 4 hours, the conversion of 2,3,5,6-tetrafluorobenzonitrile was found to be 100% and the yield of 2,3,5,6-tetrafluorobenzaldehyde (based on 2,3,5,6-tetrafluorobenzonitrile) was 84%.

Example 18
(Reaction for Conversion from Cyano Group to Aldehyde Group)

Using 91 g of methanol, 12 g of water, 45 g of acetic acid, and 0.25 g of Raney nickel, a reaction was carried out by a method similar to Example 17. When the reaction was carried out at 60° C. for 2 hours, the conversion of 2,3,5,6-tetrafluorobenzonitrile was found to be 100% and the yield of 2,3,5,6-tetrafluorobenzaldehyde (based on 2,3,5,6-tetrafluorobenzonitrile) was 70%.

Example 19
(Reaction for Conversion from Cyano Group to Aldehyde Group)

Using 82 g of dioxane, 21 g of water, 45 g of acetic acid, and 0.5 g of Raney nickel, a reaction was carried out by a method similar to Example 18. The conversion of 2,3,5,6-tetrafluorobenzonitrile was found to be 100% and the yield of 2,3,5,6-tetrafluorobenzaldehyde (based on 2,3,5,6-tetrafluorobenzonitrile) was 47%. The yield of 2,3,5,6-tetrafluorobenzyl alcohol was 2%.

Example 20
(Reaction for Conversion from Aldehyde Group to Hydroxymethyl Group)

27 g of dioxane, 9 g of acetic acid, 53 g of water, 1.5 g of Raney nickel, and 3.0 g of 2,3,5,6-tetrafluorobenzaldehyde were added to a 500 cc stainless steel autoclave equipped with a Teflon inner tube in a nitrogen atmosphere. The gas phase was sufficiently replaced with hydrogen gas, then the pressure was raised to 0.5 MPa (gauge pressure). The reaction was performed at 50° C. for 2 hours, then the reaction solution was analyzed by gas chromatography, whereupon the conversion of 2,3,5,6-tetrafluorobenzaldehyde was found to be 100% and the yield of 2,3,5,6-tetrafluorobenzyl alcohol (based on 2,3,5,6-tetrafluorobenzaldehyde) was 99%.

Example 21
(Reaction for Conversion from Aldehyde Group to Hydroxymethyl Group)

A reaction was carried out in the same way as in Example 20, except that 33 g of methanol, 18 g of acetic acid, 8 g of water, and 2.0 g of 2,3,5,6-tetrafluorobenzaldehyde were used and the reaction temperature was made 80° C. The conversion of 2,3,5,6-tetrafluorobenzaldehyde was found to be 81% and the yield of 2,3,5,6-tetrafluorobenzyl alcohol (based on 2,3,5,6-tetrafluorobenzaldehyde) was 81%.

Example 22
(Reaction for Conversion from Cyano Group to Hydroxymethyl Group)

83 g of methanol, 45 g of acetic acid, 21 g of water, 0.5 g of Raney nickel, and 5.0 g of 2,3,5,6-tetrafluorobenzonitrile were added to a 500 cc stainless steel autoclave equipped with a Teflon inner tube in a nitrogen atmosphere. The gas phase was sufficiently replaced with hydrogen gas, then the autoclave was sealed and heated to 60° C. The reaction was carried out for 2 hours, Next, 1.0 g of Raney nickel catalyst was newly added, the gas sufficiently replaced with hydrogen gas, then the pressure raised to 0.5 MPa (gauge pressure). The reaction was carried out at 80° C. for 2 hours again, then the reaction solution was analyzed by gas chromatography, whereupon the conversion of 2,3,5,6-tetrafluorobenzonitrile was found to be 100%, the yield of 2,3,5,6-tetrafluorobenzyl alcohol (based on 2,3,5,6-tetrafluorobenzonitrile) was 57%, and the yield of 2,3,5,6-tetrafluorobenzaldehyde was 2%.

Example 23
(Reaction for Conversion from Cyano Group to Hydroxymethyl Group)

2.5 g of Raney nickel and 0.65 g of lead acetate were added and a reaction was carried out by a method similar to Example 22 for 2.5 hours. Without further adding a catalyst, this is pressurized with hydrogen gas to 0.5 MPa (gauge pressure) as it is and the reaction again performed at 80° C. for 2 hours, whereupon the conversion of 2,3,5,6-tetrafluorobenzonitrile was found to be 100%, the yield of 2,3,5,6-tetrafluorobenzyl alcohol (based on 2,3,5,6-tetrafluorobenzonitrile) was 48%, and the yield of 2,3,5,6-tetrafluorobenzaldehyde was 1%.

Industrial Applicability

According to the present invention, it is possible to produce the fluorinated benzyl alcohol having the general formula (I) and the fluorinated benzonitrile having the general formula (III) by an industrially advantageous method at a high yield. In particular, it is possible to produce 2,3,5,6-tetrafluorobenzonitrile and 2,3,5,6-tetrafluorobenzyl alcohol useful as production intermediates of pyrethroids.

We claim:

1. A process for producing a fluorinated benzonitrile comprising the step of:

hydrogenolyzing a fluorinated dicyanobenzene substituted with 1 to 4 fluorine atoms and having the remainder which may be substituted with a chlorine atom in the presence of at least one metal catalyst selected from the group consisting of metals of Group VIII, Group IX, and Group X of the Periodic Table with or without supplying hydrogen gas using an aromatic compound having hydrogen at its α-position as a source of hydrogen at a temperature from room temperature to about 400° C. so as to cause hydrodecyanation of only the cyano group.

2. A process for producing a fluorinated benzonitrile as claimed in claim 1, wherein the catalyst is at least one metal catalyst selected from the group consisting of metals of Group VIII, Group IX, and Group X of the Periodic Table.

3. A process for producing a fluorinated benzonitrile as claimed in claim 1, wherein the fluorinated dicyanobenzene is tetrafluoroterephthalonitrile.

4. A process for producing a fluorinated benzonitrile as claimed in claim 1, wherein a monoalkyl substituted benzene is used as the solvent.

5. A process for producing a fluorinated benzonitrile as claimed in claim 1, wherein the hydrodecyanation reaction is carried out with or without supplying hydrogen gas using an aromatic compound having hydrogen at its α-position as a source of hydrogen.

6. A process for producing a fluorinated benzyl alcohol having the formula (I):

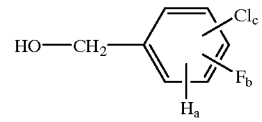

wherein a and b independently represent 1, 2, 3, or 4 and c represents 0, 1, or 2 comprising the steps of:

hydrodecyanating only one of the cyano groups of a fluorinated dicyanobenzene having the formula (II)

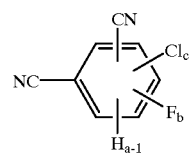

wherein a, b, and c are defined as above, to produce a fluorinated benzonitrile having the formula (III):

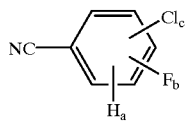

wherein a, b, and c are as defined above and then
converting the cyano group of the fluorinated benzonitrile to a hydroxymethyl group.

7. A process for producing a fluorinated benzyl alcohol as claimed in claim 6, wherein the process comprises hydrogenolyzing the fluorinated dicyanobenzene having the above formula (II) in the presence of a catalyst to hydrodecyanate only one cyano group, whereby the fluorinated benzonitrile having the formula (III) is produced, and then reducing the resultant fluorinated benzonitrile or hydrolyzing the resultant fluorinated benzonitrile and reducing the resultant corresponding fluorinated benzoic acid thereby to convert the cyano group to a hydroxymethyl group.

8. A process for producing a fluorinated benzyl alcohol as claimed in claim 7, wherein the catalyst is at least one metal catalyst selected from the group consisting of metals of Group VIII, Group IX, and Group X of the Periodic Table.

9. A process for producing a fluorinated benzyl alcohol as claimed in claim 6, wherein the fluorinated dicyanobenzene is tetrafluoroterephthalonitrile.

10. A process for producing a fluorinated benzyl alcohol as claimed in claim 6, wherein the fluorinated benzonitrile having the formula (III) is reduced to a fluorinated benzaldehyde having the formula:

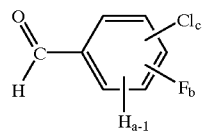

(IV)

wherein a, b, and c are as defined above, and the aldehyde group of the fluorinated benzaldehyde is then reduced to a hydroxymethyl group.

11. A process for producing a fluorinated benzyl alcohol as claimed in claim 10, wherein the cyano group of the fluorinated benzonitrile having the above formula (III) is reduced to a hydroxymethyl group by a single stage reaction without isolating the fluorinated benzaldehyde.

12. A process for producing a fluorinated benzyl alcohol as claimed in claim 6, wherein tetrafluoroterephthalonitrile is used as a starting material and only the cyano group of one side is hydrodecyanated to produce 2,3,5,6-tetrafluorobenzonitrile, followed by converting the cyano group of the 2,3,5,6-tetrafluorobenzonitrile to a hydroxymethyl group so as to produce 2,3,5,6-tetrafluorobenzyl alcohol.

13. A process for producing a fluorinated benzyl alcohol as claimed in claim 6, wherein a monoalkyl substituted benzene is used as a solvent of the hydrodecyanation reaction.

14. A process for producing a fluorinated benzyl alcohol as claimed in claim 6, wherein the hydrodecyanation reaction is carried out with or without supplying hydrogen gas using an aromatic compound having hydrogen at its α-position as a source of hydrogen.

15. A process for producing a fluorinated benzyl alcohol comprising the step of:

reducing a fluorinated benzonitrile substituted with 1 to 4 fluorine atoms and having the remainder which may be substituted with a chlorine atom or hydrolyzing the fluorinated benzonitrile and reducing the resultant corresponding fluorinated benzoic acid to convert the cyano group to a hydroxymethyl group.

16. A process for producing a fluorinated benzyl alcohol as claimed in claim 15, wherein the fluorinated benzonitrile is 2,3,5,6-tetrafluorobenzonitrile.

* * * * *